US006808684B2

(12) United States Patent
Boden et al.

(10) Patent No.: US 6,808,684 B2
(45) Date of Patent: Oct. 26, 2004

(54) FRAGRANCE MATERIAL

(75) Inventors: Richard M. Boden, Ocean, NJ (US); Irene Christine Burtyk, Westfield, NJ (US); Vito Joseph Mancini, Summit, NJ (US); Iku Sasaki, Demarest, NJ (US)

(73) Assignee: International Flavors & Fragrance Inc., New York, NY (US)

( * ) Notice: Subject to any disclaimer, the term of this patent is extended or adjusted under 35 U.S.C. 154(b) by 222 days.

(21) Appl. No.: 10/117,479

(22) Filed: Apr. 5, 2002

(65) Prior Publication Data

US 2003/0190267 A1 Oct. 9, 2003

(51) Int. Cl.$^7$ ................................................ A61L 9/01
(52) U.S. Cl. ........................ 422/124; 422/125; 512/2; 424/76.2
(58) Field of Search ............................ 422/5, 124, 125; 512/1, 2; 424/76.2

(56) References Cited

U.S. PATENT DOCUMENTS

| | | |
|---|---|---|
| 1,994,932 A | 3/1935 | Vidal |
| 2,597,195 A | 5/1952 | Smith |
| 2,802,695 A | 8/1957 | Johnson |
| 3,288,556 A | 11/1966 | Weber III |
| 3,431,393 A | 3/1969 | Katsuda |
| 3,482,929 A | 12/1969 | Gentil |
| 3,550,853 A | 12/1970 | Gray |
| 3,633,881 A | 1/1972 | Yurdin |
| 4,020,321 A | 4/1977 | Oswald |
| 4,286,754 A | 9/1981 | Jones |
| 4,413,779 A | 11/1983 | Santini |
| 4,454,987 A | 6/1984 | Mitchell |
| 4,534,891 A | 8/1985 | Boden et al. |
| 4,913,350 A | 4/1990 | Purzycki |
| 4,968,487 A | 11/1990 | Yamamoto et al. |
| 5,000,383 A | 3/1991 | van der Heijden |
| 5,038,394 A | 8/1991 | Hasegawa et al. |
| 5,290,546 A | 3/1994 | Hasegawa et al. |
| 5,364,027 A | 11/1994 | Kuhn |
| 5,903,710 A | 5/1999 | Wefler et al. |
| 5,945,094 A | 8/1999 | Martin et al. |
| 5,976,503 A | 11/1999 | Martin et al. |
| 6,123,935 A | 9/2000 | Wefler et al. |
| 6,238,646 B1 | 5/2001 | Zembrodt |
| 6,293,474 B1 | 9/2001 | Helf et al. |
| 6,296,196 B1 | 10/2001 | Denen et al. |
| 6,378,780 B1 | 4/2002 | Martens, III et al. |
| 6,382,522 B2 | 5/2002 | Tomkins et al. |
| 6,386,462 B1 | 5/2002 | Martens, III |

FOREIGN PATENT DOCUMENTS

| | | | |
|---|---|---|---|
| JP | 06219932 A2 | * | 8/1994 |
| JP | 11128331 A | * | 5/1999 |
| JP | 11332969 A2 | * | 12/1999 |
| WO | WO 96/28497 | | 9/1996 |
| WO | WO 99/01106 A1 | * | 1/1999 |
| WO | WO 02/089861 A1 | | 11/2002 |

* cited by examiner

Primary Examiner—Elizabeth McKane
(74) Attorney, Agent, or Firm—Joseph F. Leightner

(57) ABSTRACT

Non-aqueous based fragrance compositions containing a siloxane material are disclosed. The fragrance compositions are suitable for many applications including cosmetics, laundry care and personal care items. The fragrance compositions can also be used in air fresheners, particularly those air fresheners that contain heating elements.

8 Claims, No Drawings

FRAGRANCE MATERIAL

FIELD OF THE INVENTION

This application is directed to fragrance materials containing silicones, particularly fragrance materials containing siloxanes in a non-aqueous based fragrance system.

BACKGROUND OF THE INVENTION

Most fragrance chemicals are hydrophobic materials indicating that they are more soluble in non-aqueous based systems than aqueous systems. For this reason, fragrance compositions are commonly provided in a hydrocarbon base. These hydrocarbon bases comprise materials including alcohols, such as ethanol, and other materials, such as dipropylene glycol and diethyl phthlatae and isopropyl myristate. Higher boiling solvents can also be used in systems depending on the application and are commonly provided in a non-aqueous based systems. Higher temperature applications include plug-in air fresheners where the electric power source can be used to power a heating element to deliver the fragrance chemicals and a higher boiling fragrance solvents. In these situations higher boiling point carriers such as dipropylene glycol ethers are often used as the fragrance chemical solvents.

Alternatively, an aqueous based system may be employed to deliver fragrance materials. One advantage of an aqueous based fragrance system is the reduced flash point of the fragrance system. In order to make the fragrance chemicals miscible and deliverable in the aqueous system, surfactant and other chemicals are used. For example, U.S. Pat. No. 6,238,646, the contents hereby incorporated by reference, discloses the use of a polymeric emulsion with a dispersed oil phase for the deliverance of atomized oil, such as a fragrance oil, insecticidal oil or medicinal oil. The patent states that the dispersed oil has the benefits of not needing to be shaken before use, is not flammable and does not deposit fragrance on surfaces.

The deposition of fragrance on surfaces is a problem with many fragrance systems. Controlling the rate of fragrance usage, the particle size of the fragrance as well as insuring that the fragrance remains in the atmosphere is critical. In particular for air fresheners, it is critical that the fragrance not deposit on surfaces such as tables and other surfaces leaving unsightly appearance or damage surfaces.

Despite the teachings, there is an ongoing need for new fragrance compositions that deliver the desired fragrance in a safe manner that does not deposit fragrance on surfaces after use.

SUMMARY OF THE INVENTION

The present invention is directed to a non-aqueous based fragrance system containing a siloxane oil for the delivery of fragrance chemicals. The fragrance chemical system is particularly well suited for the delivery of fragrance chemicals for air fresheners.

More specifically the present invention is directed to a liquid, non-aqueous based fragrance containing a siloxane oil at a level of from about 20 to about 30 weight percent of the fragrance composition. Preferably the siloxane oil has a vapor pressure of from about 0.8 to about 1.2 mm Hg (millimeters of mercury).

In a more preferred embodiment of the invention, a fragrance composition is provided comprising:

from about 20 to about 30 weight percent of the fragrance composition has a vapor pressure of greater than 0.3;

from about 15 to about 25 weight percent of the fragrance composition has a vapor pressure of from about 0.1 to about 0.3;

from about 3 to about 12 weight percent of the fragrance composition has a vapor pressure of from 0.03 to about 0.01; and less than about 10 weight percent of the fragrance composition has a vapor pressure of less than 0.01; and a siloxane oil from about 20 to about 30 weight of the fragrance.

In a highly preferred embodiment of the invention, a fragrance composition is provided comprising:

from about 23 to about 28 weight percent of the fragrance composition has a vapor pressure of greater than 0.3;

from about 16 to about 20 weight percent of the fragrance composition has a vapor pressure of from about 0.1 to about 0.3;

from about 4 to about 6 weight percent of the fragrance composition has a vapor pressure of from 0.03 to about 0.01; and less than 5, more preferably from about 0.01 to about 4 weight percent of the fragrance composition having a vapor pressure of less than 0.01; and a siloxane oil from about 23 to about 28 weight of the fragrance.

The present invention is also directed to a method and apparatus for delivering fragrance from an air freshener, the air freshener containing a heating element preferably with a piezo electric device.

The above embodiments and other embodiments of the present invention will become apparent from a reading of the following specification and examples.

DETAILED DESCRIPTION OF THE INVENTION

The selection of the appropriate fragrance materials and non-aqueous carrier of the present invention is critical. The fragrance materials and carriers must have the vapor pressure distribution in order to be effective in the present invention. Failure to provide the appropriate vapor pressure characteristics can lead to the same problems discussed herein above.

The appropriate carrier materials include but are not limited to alcohols such as ethanol, methanol, and the like; dipropylene glycol, dipropylene glycol ethers, diethyl phthalate and isopropyl myristate. The level of water in these systems is intentionally kept to a minimum, preferably below 5 weight percent of the fragrance composition, more preferably below 1 weight percent and most preferably less than 0.1 weight percent. Persons with skill in the art will be able to formulate fragrance compositions within the scope of the present invention that contain no intentionally added water.

The level of non-aqueous basis in the fragrance can vary widely from as little as 0.01 to about 50 weight percent of the total fragrance composition. More commonly, the level of the fragrance base is from about 5 to about 30 weight percent, more preferably from about 10 to about 25 and in a highly preferred level from about 15 to about 25 weight percent of the fragrance composition.

The siloxane materials of the present invention are provided at a level of from 20 to about 30; preferably from about 23 to about 28 and most preferably from about 24 to about 26 weight percent of the fragrance composition.

The siloxane materials suitable for use in this invention is an organo-silicon polymer with a silicon-oxygen framework with a simplest fundamental unit of $(R_2SiO)n$. As used in this application, siloxane materials include both siloxane and silicone materials. The siloxane materials can be straight chains or branched, with multiple branching possible both in the polymer chain as well as in the end groups.

The siloxane materials that are incorporated in the present invention are typically characterized by their molecular weight. Suitable materials have molecular weights ranging from about 150 to about 400; preferably from about 290 to about 390; and most preferably from about 295 to about 320.

Siloxane materials that have been found to be suitable in the present invention, include but are not limited to decamethyltetrasiloxane, octamethylcyclotetrasiloxane, hexamethyltetrasiloxane, polydimethylsiloxane, and the like. The most preferred materials for use in this invention are decamethyltetrasiloxane and octamethylcyclotetrasiloxane.

The vapor pressure of the siloxane-containing fragrance materials of the present invention varies from about 0.5 to about 2, preferably from about 0.8 to about 1.2 and most preferably 1.0. As used in this specification, the vapor pressure of the materials is measured at 25° C. and at 760 millimeters of mercury. Vapor pressure of the materials is measured by ASTM D5191, ASTM D323, ASTM D4953. As used throughout the specification, ASTM is understood to be the test methods promulgated by American Society for Testing Materials, 100 Barr Harbor Drive, PO Box C700, West Conshocken, Pa. 19428. The number following the ASTM name designates the test method for determining the physical parameter. In addition to determining vapor pressures, vapor pressures can be found in various reference books, such as, CRC *Handbook of Chemicals and Physics*, various editions; and *Chemical Properties Handbook*, Yaw, Carl L., editor; McGraw-Hill Publishing Company, 1999.

The viscosity of the fragrance composition, including the non-aqueous base, the fragrance chemicals and the silicon or siloxane materials should be less than about 2 centipoise, preferably from about 0.25 to about 1.5 centipoise, most preferably from about 0.5 to about 1.25 centipoise. Highly preferred fragrance materials have a viscosity of about 1 centipoise as measured at 25° C. and at 25 revolutions per minute using a number 2 spindle.

The fragrance composition should have a flash point of less than 200° F., preferably from about 140 to about 180 and most preferably from about 140 to about 160° F. Flash point is measured by ASTM D 6450.

The fragrance chemicals used in the practice of the present invention are not critical as long as the resulting fragrance composition has the vapor pressure distribution recited herein. Of course, the aesthetic consideration of any fragrance composition is critical to the commercial success of the fragrance.

For example, fragrance chemicals having a vapor pressure of greater than 0.3 mm Hg include but are not limited to: allyl acetone, ethyl amyl ketone, furfural, iso amyl acetate, iso butyl butyrate, methyl furoate, methyl disulfide, propanal, proponol, propyl acetate, hexyl acetate, ethyl acetoacetate, citrus oil distillate, tetrahydrolinalool, and the like.

Similarly, fragrance chemicals having a vapor pressure of form about 0.1 to about 0.3 include, but are not limited to: allyl caproate, dimethyl octanol, isoamyl crotonate, rose oxide, methyl benzoxalate, methyl heptyl ketone, nonyl aldehyde, benzyl acetate and Vanoris® (IFF) and the like.

Fragrance chemicals having a vapor pressure of from about 0.03 to about 0.1 mm Hg include, but are not limited to: benzoic acid, cyclohexyl propanol, diethyl succinate, dimethyl octanol, isobutyl caproate, methyl chavicol, oxane, Verdox® (IFF), Vertenex HC® (IFF), phenyl acetaldehyde dimethylacetal, citronellyl acetate and dihydrocarvone and the like.

Fragrance chemicals having a vapor pressure of from about 0.01 to about 0.03 mm Hg include, but are not limited to: allyl amyl glycolate, anisic alcohol, benzyl isobutyrate, hexenyl isobutyrate, hexyl crotonate, phenoxy ethanol, nonyl alcohol, and the like.

Fragrance chemicals having a vapor pressure of less than 0.01 mm Hg include, but are not limited to: allyl caproate, anisyl acetate, ethyl anisole, hexyl caproate, Iso E Superb® (IFF), methyl iritone, phenoxy ethyl iso butyrate, yara yara, citronellyl acetate, and Vertenex® (IFF) and the like.

The vapor pressure of fragrance chemicals is available from reference materials such as the CRC Handbook of Chemistry and Physics, various editions; or can be determined by ASTM D5191, ASTM D323, and ASTM D4953.

Fragrance chemicals are well known in the art. A list of suitable fragrances is provided in U.S. Pat. No. 4,534,891, the contents of which are incorporated by reference as if set forth in their entirety. Another source of suitable fragrances is found in *Perfumes Cosmetics and Soaps*, Second Edition, edited by W. A. Poucher, 1959. Among the fragrances provided in this treatise are acacia, cassie, chypre, cylamen, fern, gardenia, hawthorn, heliotrope, honeysuckle, hyacinth, jasmine, lilac, lily, magnolia, mimosa, narcissus, freshly-cut hay, orange blossom, orchids, reseda, sweet pea, trefle, tuberose, vanilla, violet, wallflower, and the like.

As used in this specification olfactory effective amount is understood to mean the amount of fragrance materials in perfume composition that has an effect on the overall fragrance. As is well appreciated in the art, the individual component will contribute its particular olfactory characteristics, but the olfactory effect of the fragrance will be the sum of the effects of each of the perfume or fragrance ingredients. Thus the fragrance materials can be used to alter the aroma characteristics of the fragrance, or by modifying the olfactory reaction contributed by another ingredient in the composition. The amount will vary depending on many factors including other ingredients, their relative amounts and the effect that is desired.

The level of siloxane containing fragrance used to scent an article typically varies from about 0.005 to about 20 weight percent, preferably from about 0.5 to about 15 and most preferably from about 1 to about 10 weight percent. Those with skill in the art will be able to employ the desired level of the fragrance compositions of the invention to provide the desired fragrance and intensity to a wide variety of products.

The use of these compounds is widely applicable in current perfumery products, including the preparation of perfumes and colognes, the perfuming of personal care products such as soaps, shower gels, and hair care products as well as cosmetic preparations. The present invention can also be used to perfume cleaning agents, such as, but not limited to detergents, dishwashing materials, scrubbing compositions, window cleaners and the like.

The siloxane-containing fragrance materials of the present invention are particularly well suited for use in air fresheners, which are known in the art, see for example U.S. Pat. Nos. 1,994,932; 2,597,195; 2,802,695; 2,804,291;

3,550,853; 4,286,754; 4,413,779; 4,454,987; 4,913,350; and 5,000,383 hereby incorporated by reference.

The present invention is particularly well-suited for air fresheners that are powered by an electrical source. The electrical source is typically used to power a heating element that promotes the evaporation of the fragrance materials. These devices are also well known in the art, see for example, U.S. Pat. Nos. 3,288,556; 3,431,393; 3,482,929; 3,633,881; 4,020,321; 4,968,487; 5,038,394; 5,290,546 and 5,364,027, incorporated by reference. In a preferred embodiment, the air freshener contains a piezo electric element.

Well known materials such as surfactants, emulsifiers, extenders can also be employed without departing from the scope of the present invention. The present invention is provided in a liquid form, the fragrance is not encapsulated by a polymer, gelatin or other material that would inhibit the effects the vapor pressure distribution of the fragrance chemicals has on the overall fragrance composition.

The present invention possesses a number of advantages over previous fragrance compositions. The fragrance materials possess improved evaporative properties, meaning that better droplet formation is created. In addition, the fragrance does not redeposit on surfaces after being released into the atmosphere and the fragrance materials have a flash point that is safe for the materials to be used with devices that contain a heating element.

In view of the above description and the following example, a person with ordinary skill in the art will understand that other modifications and embodiments may be derived without departing from the spirit and scope of this invention. Unless noted to the contrary, all units set forth below are weight percent.

EXAMPLE 1

The following fragrance formulation was prepared to demonstrate the distribution of vapor pressure of individual ingredients and relative weight percent suitable for use in the present invention. The fragrance was reported to have a citrus aroma.

| CHEMICAL | VAPOR PRESSURE (mm Hg) | WEIGHT % |
|---|---|---|
| Decamethyltetramethylsiloxane (Aldrich Chemical) | 1 | 26.49 |
| Hexylacetate | 1 | 2.92 |
| Citrus Oil Dist | 0.9 | 9.79 |
| Ethyl Acetoacetate | 0.5 | 6.16 |
| Tetrahydrolinalool | 0.4 | 5.44 |
| Benzyl Acetate | 0.1 | 14.55 |
| Vanoris ® (IFF) | 0.053 | 3.62 |
| Dihydromyrencol | 0.09 | 5.44 |
| Isobornyl Acetate | 0.09 | 3.62 |
| Linalool | 0.05 | 4.28 |
| Verdox ® (IFF) | 0.05 | 2.46 |
| Vertenex HC ® (IFF) | 0.04 | 3.12 |
| Cyclacet ® (IFF) | 0.02 | 1.08 |
| Phenylacetaldehyde dimethylacetal | 0.02 | 1.81 |
| Citronellyl Acetate | 0.01 | 1.45 |
| Dihydrocyclacet ® (IFF) | 0.008 | 1.08 |

All of the above fragrance chemicals are available from International Flavors & Fragrances Inc. (IFF), Hazlet, NJ.

EXAMPLE 2

Several fragrance compositions were prepared having the viscosity and flash point set forth below. All vapor pressure values are mm Hg.

| | Citus | Emerald Green | Wildflower | Apple | Ivory | Floral | Desire |
|---|---|---|---|---|---|---|---|
| Viscosity (Centipoise) | 1.64 | 1.97 | 1.87 | 1.71 | 1.63 | 1.80 | 1.65 |
| Flash Point (° F.) | 148 | 150 | 152 | 147 | 145 | 148 | 148 |
| Weight percent of fragrance chemicals with vapor pressure greater than 0.3 | 26.77 | 26.44 | 24.43 | 27.06 | 27.4 | 24.77 | 27.05 |
| Weight percent of fragrance chemicals with vapor pressure between 0.3 and 0.1 | 18.70 | 18.15 | 14.66 | 18.82 | 19.75 | 17.93 | 19.35 |
| Weight percent of fragrance chemicals with vapor pressure between 0.1 and 0.03 | 19.97 | 22.03 | 26.67 | 22.34 | 18.10 | 19.62 | 20.02 |
| Weight percent of fragrance chemicals with vapor pressure between 0.03 and 0.01 | 6.10 | 6.57 | 8.30 | 5.85 | 2.25 | 11.68 | 5.58 |
| Weight percent of fragrance chemicals with vapor pressure less than 0.01 | 1.10 | 0.57 | 0.02 | 0.50 | 2.30 | 0.80 | 0.80 |
| Siloxane oil level | 26.49 | 25.00 | 25.00 | 25.00 | 30.00 | 25.00 | 27.00 |

Due to rounding the numbers do not total to 100.

The fragrance compositions were placed in an electrically powered air freshener device. The air freshener device was turned on and the fragrance compositions were provided into the atmosphere. The devices were periodically evaluated for the delivery of fragrance and other criteria.

It was noted that the floral fragrance had an unacceptably large amount of fragrance that had deposited onto the table surface. It is believed that the level of fragrance materials having a vapor pressure of from 0.01 to 0.03 being 11.68 weight percent was the cause. This fragrance composition does not have the vapor pressure distribution recited in the claims. The other fragrance compositions delivered the fragrances to the atmosphere in a satisfactory manner without the problem of the fragrance chemicals redepositing on the tabletop. The other fragrances had the vapor pressure distribution and siloxane oil levels recited in the claims.

We claim:

1. A liquid, non-aqueous based fragrance composition comprising:
   from about 20 to about 30 weight percent of the fragrance composition having a vapor pressure of greater than 0.3;
   from about 15 to about 25 weight percent of the fragrance composition having a vapor pressure of from about 0.1 to about 0.3;
   from about 15 to about 25 weight percent of the fragrance composition having a vapor pressure of from 0.03 to about 0.1;
   from about 3 to about 9 weight percent of the fragrance composition having a vapor pressure of from 0.01 to about 0.03; and
   less than about 10 weight percent of the fragrance having a vapor pressure of less than 0.01;
   and a siloxane oil from about 20 to about 30 weight percent of the fragrance composition.

2. The fragrance composition of claim 1 wherein the siloxane oil is selected from the group consisting of decamethyltetrasiloxane, octamethylcyclotetrasiloxane, hexamethyltetrasiloxane, and polydimethylsiloxane.

3. The fragrance composition of claim 2 wherein the fragrance composition has a viscosity of less than about 2 centipoise.

4. The fragrance composition of claim 3 wherein the fragrance composition has a viscosity of from about 0.5 to about 1.5 centipoise.

5. A liquid, non-aqueous based fragrance composition comprising:
   from about 23 to about 38 weight percent of the fragrance composition having a vapor pressure of greater than 0.3;
   from about 16 to about 20 weight percent of the fragrance composition having a vapor pressure of from about 0.1 to about 0.3;
   from about 4 to about 6 weight percent of the fragrance has a vapor pressure of from 0.03 to about 0.1; and
   less than about 4 weight percent of the fragrance having a vapor pressure of less than 0.01; and
   a siloxane oil from about 23 to about 28 weight percent of the fragrance.

6. An air freshener apparatus that contains the fragrance of claim 5.

7. The air freshener apparatus of claim 6 that contains a heating element.

8. The air freshener apparatus of claim 6 that contains a piezo electric element.

* * * * *